(12) United States Patent
Kovacs

(10) Patent No.: US 11,717,459 B2
(45) Date of Patent: Aug. 8, 2023

(54) SINGLE-ACTION, MULTI-DIRECTIONAL CLAMP ASSEMBLY, SYSTEM AND METHOD

(71) Applicant: INNOVATIVE MEDICAL PRODUCTS, INC., Plainville, CT (US)

(72) Inventor: Tamas Kovacs, Burlington, CT (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 0 days.

(21) Appl. No.: 17/857,535

(22) Filed: Jul. 5, 2022

(65) Prior Publication Data

US 2022/0331184 A1 Oct. 20, 2022

Related U.S. Application Data

(63) Continuation of application No. 17/073,334, filed on Oct. 17, 2020, now Pat. No. 11,400,006.

(60) Provisional application No. 62/916,674, filed on Oct. 17, 2019.

(51) Int. Cl.
*A61G 13/10* (2006.01)
*A61B 90/57* (2016.01)
*F16B 2/12* (2006.01)

(52) U.S. Cl.
CPC ............ *A61G 13/101* (2013.01); *A61B 90/57* (2016.02); *F16B 2/12* (2013.01)

(58) Field of Classification Search
CPC .......... A61G 13/101; A61B 90/57; F16B 2/12
See application file for complete search history.

(56) References Cited

U.S. PATENT DOCUMENTS

| | | | |
|---|---|---|---|
| 8,485,509 B2 * | 7/2013 | Wang | B24B 41/06 269/95 |
| 8,621,692 B1 * | 1/2014 | Kring | A61G 13/101 5/503.1 |
| 9,011,034 B2 * | 4/2015 | Liu | F24S 25/615 403/381 |
| 9,022,334 B1 * | 5/2015 | DeMayo | A61G 13/101 248/229.24 |
| 9,585,806 B2 * | 3/2017 | Herrig | A61G 13/101 |
| 11,248,634 B2 * | 2/2022 | Shetty | F16B 2/10 |
| 2022/0362084 A1 * | 11/2022 | Kovacs | A61M 25/02 |

* cited by examiner

*Primary Examiner* — Anita M King
(74) *Attorney, Agent, or Firm* — Nicholas E. Blanton, Esq.; Damian Wasserbauer, Esq.; Wasserbauer Law LLC

(57) ABSTRACT

A multi-directional, equalizer clamp device is disclosed that provides, via a single action, a way to lock multiple objects that may be disposed in different numerous directions. The clamp may also achieve clamping using numerous force factors, and may be configured to attach and secure objects, such as pins, to the side rail of a support and/or operating table via a single-point of operation. The clamp device comprises upper and lower body portions which are configured to clamp to a side rail along a primary clamping direction, and are further configured to receive objects and clamp them along a secondary clamping direction. The clamp device further comprises a control assembly, such as a knob, to facilitate and achieve simultaneous clamping along both primary and secondary clamping directions at a single point of control.

9 Claims, 10 Drawing Sheets

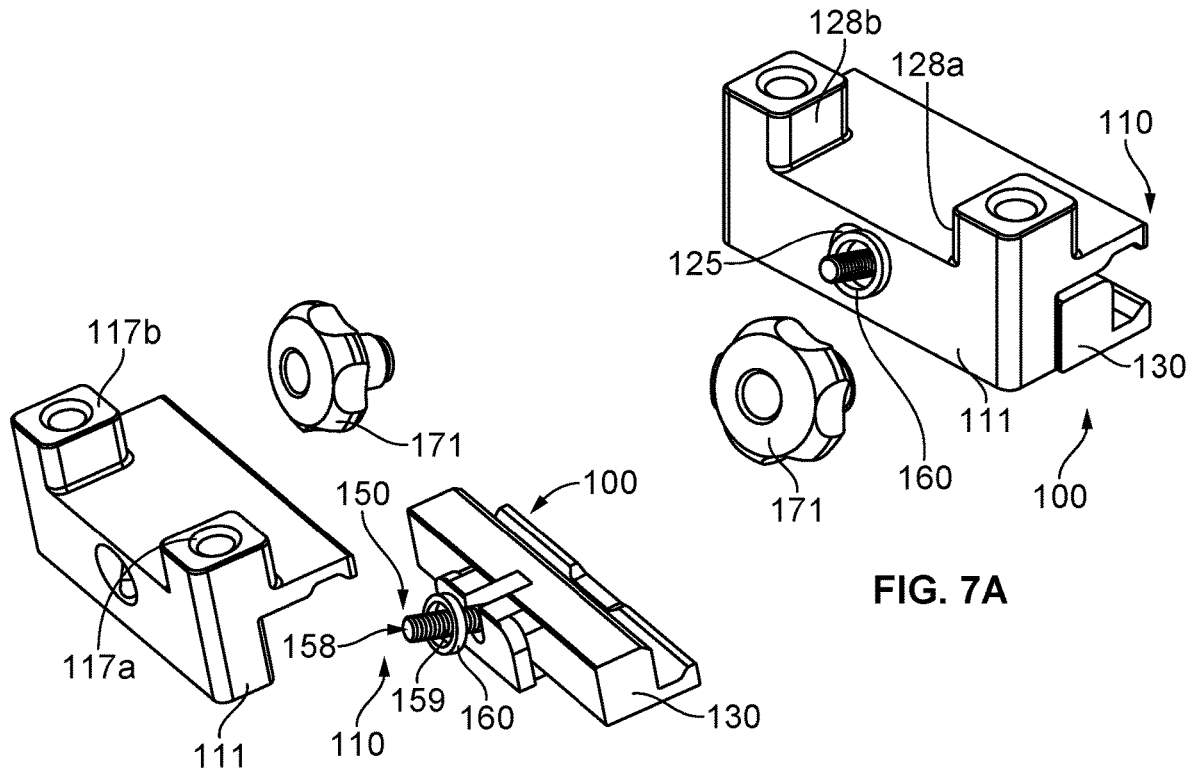
FIG. 7A
FIG. 7B
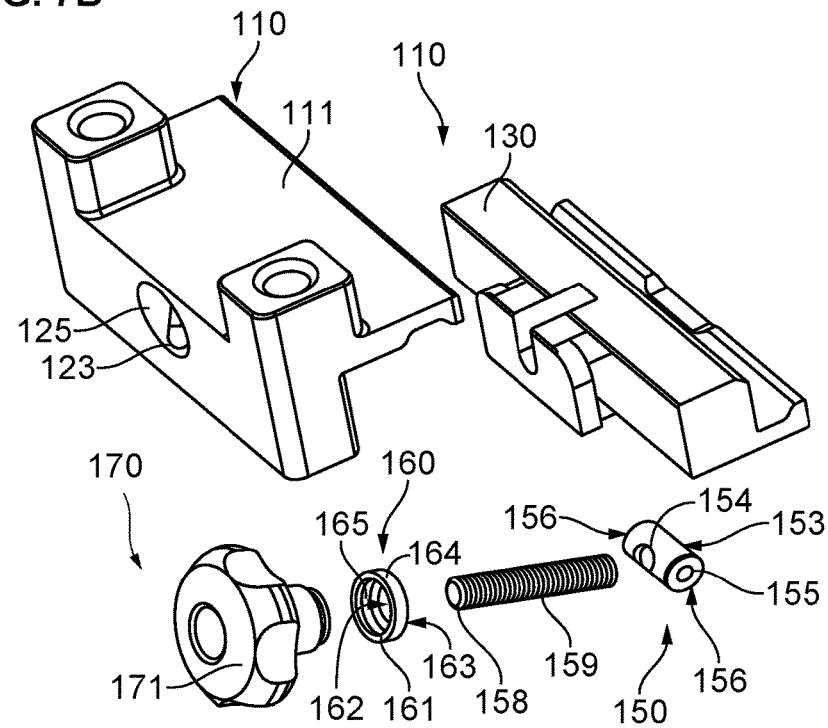
FIG. 7C

SINGLE-ACTION, MULTI-DIRECTIONAL CLAMP ASSEMBLY, SYSTEM AND METHOD

CROSS REFERENCE TO RELATED APPLICATIONS

This application is a continuation of U.S. patent application Ser. No. 17/073,334, filed Oct. 17, 2020, which claims the benefit of U.S. Provisional Application No. 62/916,674, filed Oct. 17, 2019, of which the disclosures are incorporated herein by reference in their entirely.

FIELD OF THE INVENTION

The present invention relates to a clamp assembly and, more particularly, to a clamp apparatus, system and method for a single action locking multiple components in different force factors.

BACKGROUND OF THE INVENTION

Conventional clamps are known that can clamp multiple objects to a single clamp body using individual forcing means in order to secure each object to the clamp body. For example, the clamp body may have openings to insert objects (e.g. rods, bars, standing seams, or the like) in one direction (e.g. x-plane) and other openings to insert similar objects disposed in in another direction (e.g. y-plane). For each of the opening(s) in the x-plane a forcing means is used to apply force to the clamp body such as, for example, a knob, handle, or other tightening device to urge the parts of the clamp body to tighten and/or loosen around the object. The additional components for each forcing means add complexity and cost to the manufacturing of the clamp assembly. It would be advantageous to reduce the number of components in the clamp assembly as well as to use a single forcing means to operate the clamp for multiple objects, e.g. using a single knob or handle.

Numerous applications in various industries would benefit from such a clamp assembly. For example, a clamp assembly application to attach objects to the side rail of a surgical support can improve access to the patient for the surgeon. A clamp assembly for surgical procedures further requires sterilization and improved sterilization can be accomplished with a clamp body having open channels that may be cleared by standard sterilization techniques.

Applications also exist in attaching a clamp assembly to various objects and/or structures. For example, a single action fastener that clamps multiple objects can be used advantageously in connection with a clamp assembly for the standing seam of the metal roof, thereby reducing the time of the installer on the roof and/or structure, use of available space, costs of manufacturing, and improving the aesthetic appearance of these objects installed on the structure.

Consequently, there is a need for a clamp apparatus, system and method using a fastener and/or forcing means having a single action for locking multiple objects disposed in different numerous directions that achieves clamping using numerous force factors.

BRIEF DESCRIPTION OF THE DRAWINGS

FIGS. 7A, 7B and 7C are expanded, perspective views illustrating an arrangement of the component parts of the clamp of the invention;

Figure 1:
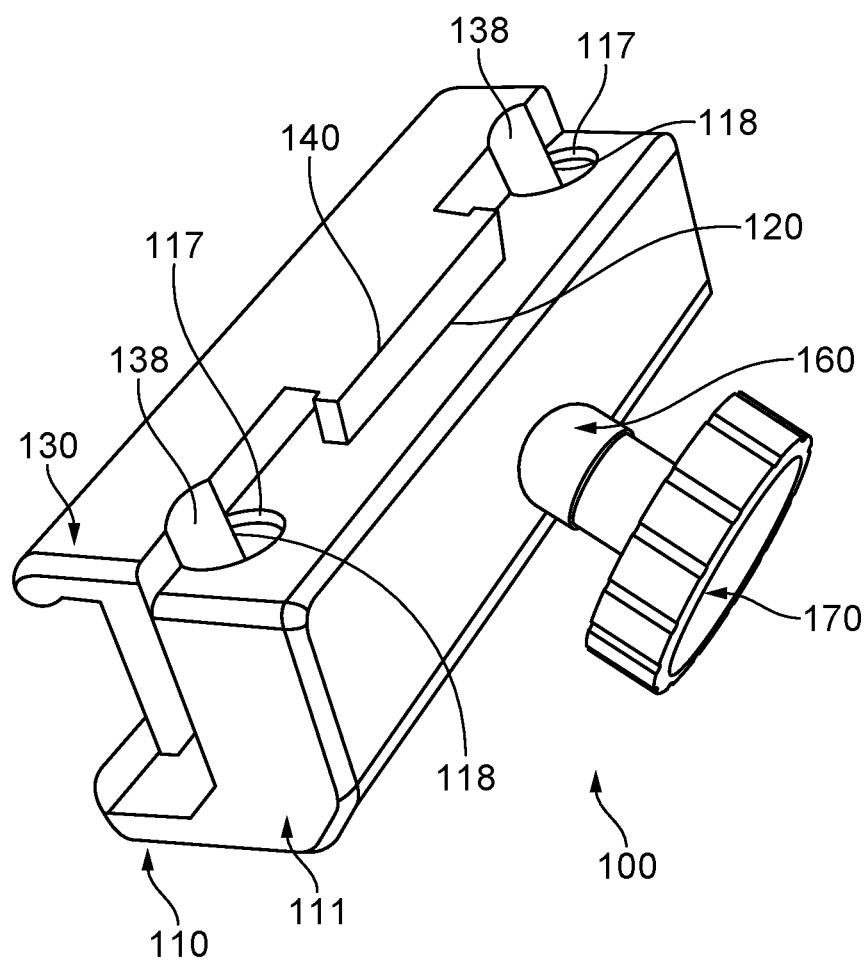
FIG. 1 illustrates a bottom, perspective view of a clamp apparatus, system, and method for a single action clamp for locking multiple objects disposed in different directions that achieves clamping using a fastener and/or forcing means having numerous force factors.

It is to be appreciated by one of skill that the clamping can be arranged on the side rail of the support table in either direction. The invention is described using an upper portion and a lower portion for the body parts of the clamp, which is merely for convenience of illustration and should not be deemed limiting to the invention in any way.

DESCRIPTION OF THE EMBODIMENTS

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (ie., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

Figure 5:
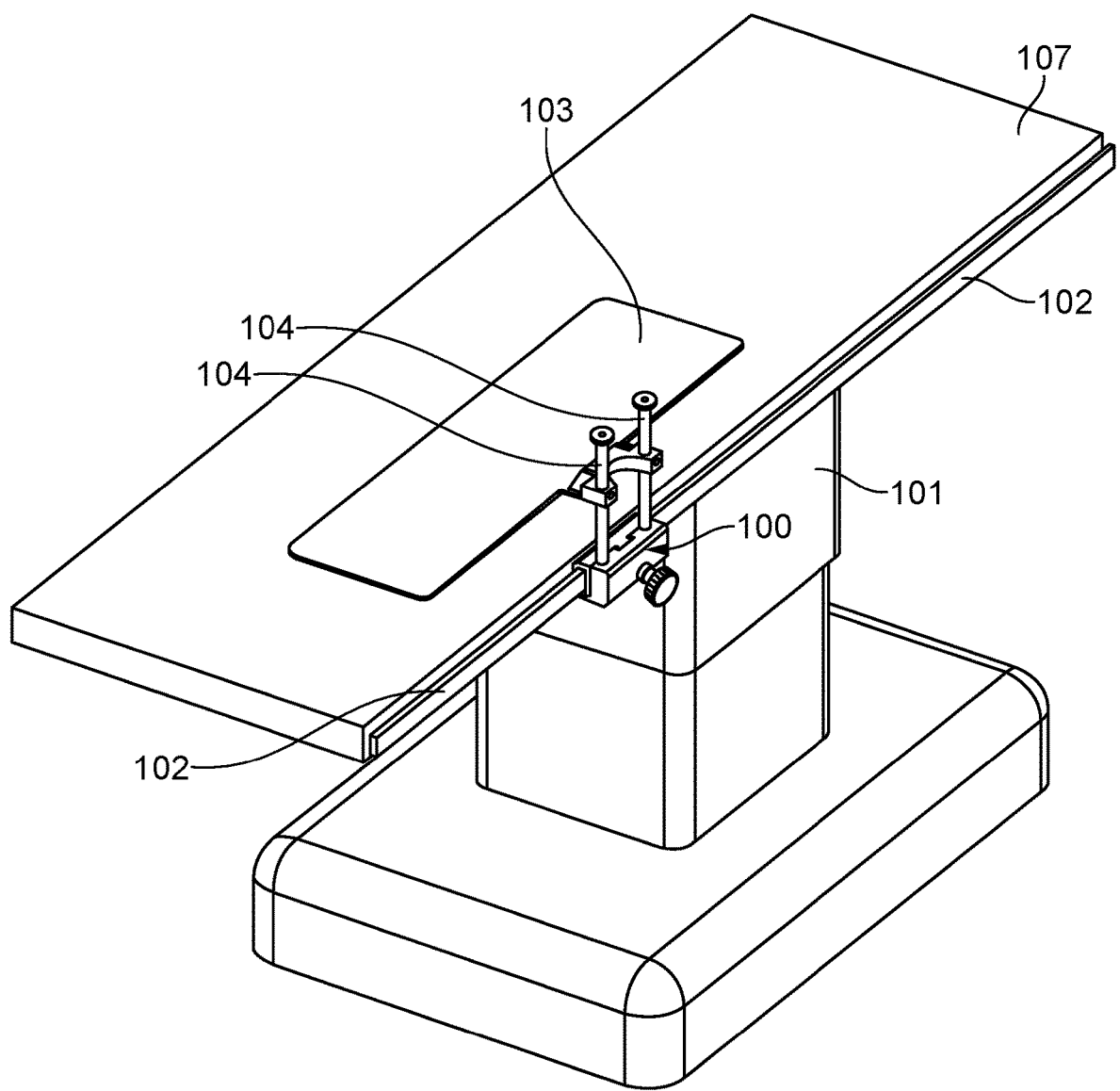
FIG. 5 illustrates an perspective view of clamp in the environment of attaching a surgical positioner using elongated posts and/or pins to a side rail of a support table, according to an embodiment of the invention.

Referring to FIGS. 1-10, a clamp apparatus, system and method for a single action locking multiple components in different force factors is generally shown as element 100. Referring to FIGS. 1-2, 6, and 7A-7C, the clamp 100 has four component parts: a clamp assembly 110, a fastener assembly 150, a washer assembly 160, and a control assembly 170. Referring to FIGS. 7A-7C, according to another embodiment of the present invention, the fastener assembly 150 may be additionally formed in two parts. As shown in FIG. 5, the clamp 100 is illustrated in the environment of attaching to a patient support 20 or operating room (OR) table 101 using the side rail 102 for attaching a patient support system 103 to a surface 107 using elongated posts and/or pins 104. The clamp 100 can be arranged on the side rail 102 of the support table 101 in either direction, up or down, switching the designation of the body components of upper portion and a lower portion, which is merely for convenience of illustration and should not be deemed limiting to the 25 invention in any way. As will be appreciated by one skilled in the art, the clamp apparatus, system and method 100 may find further used for other applications to clamp other items and things including mounting to a structure such as a metal roof, wall, building or rooftop, shingled roof, and other structures. Such items of industrial usefulness and/or known to one skilled in the art, may include conventional items mounted to a structure such as solar panels, a snow rail, HVAC equipment and/or electrical equipment.

Figure 3:
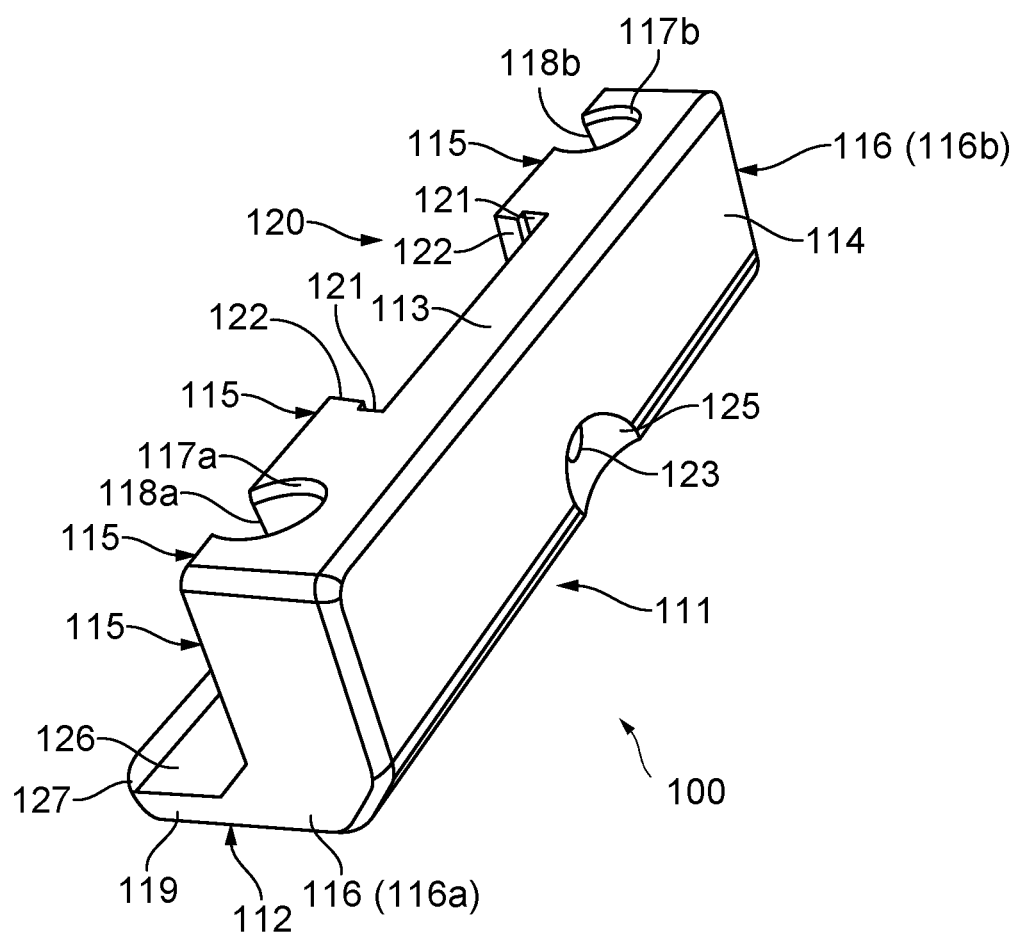
FIG. 3 illustrates a bottom, perspective view of an upper portion of the body of the clamp of the invention.
Figure 4:
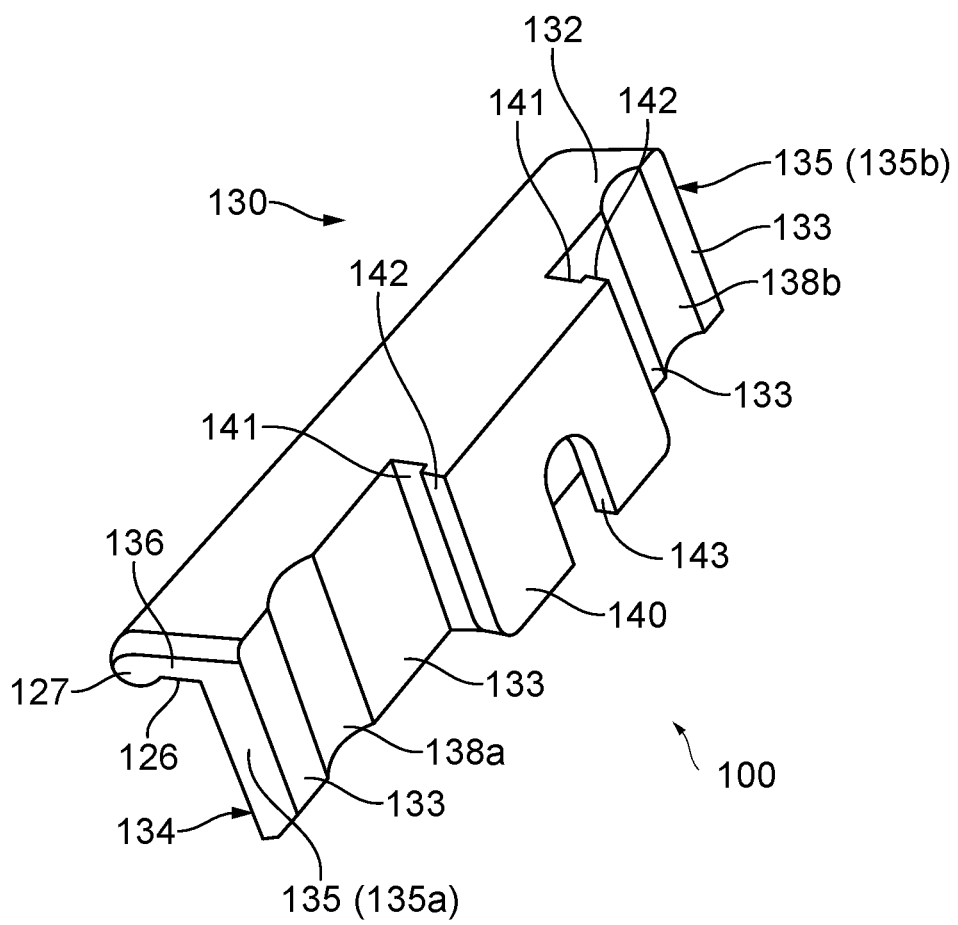
FIG. 4 illustrates a perspective view of a lower portion of the body of the clamp of the invention.
Figure 8:
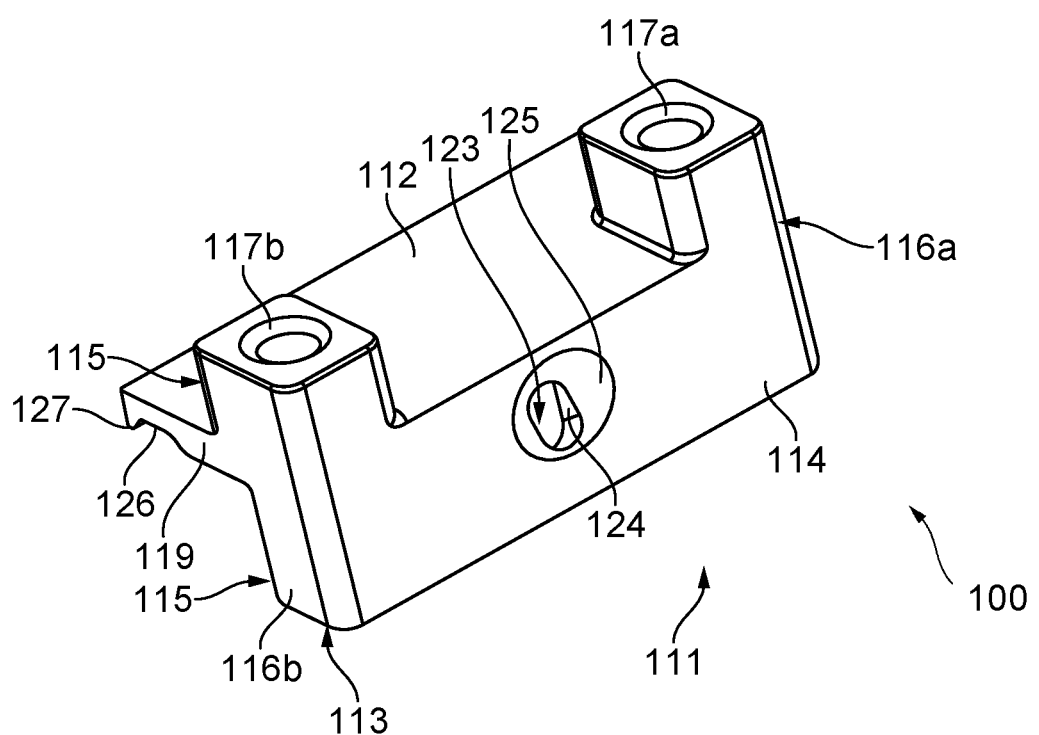
FIG. 8 illustrates a top, perspective view of upper portion of the body of the clamp using raised attachment lugs, according to an additional embodiment of the invention.
Figure 9:
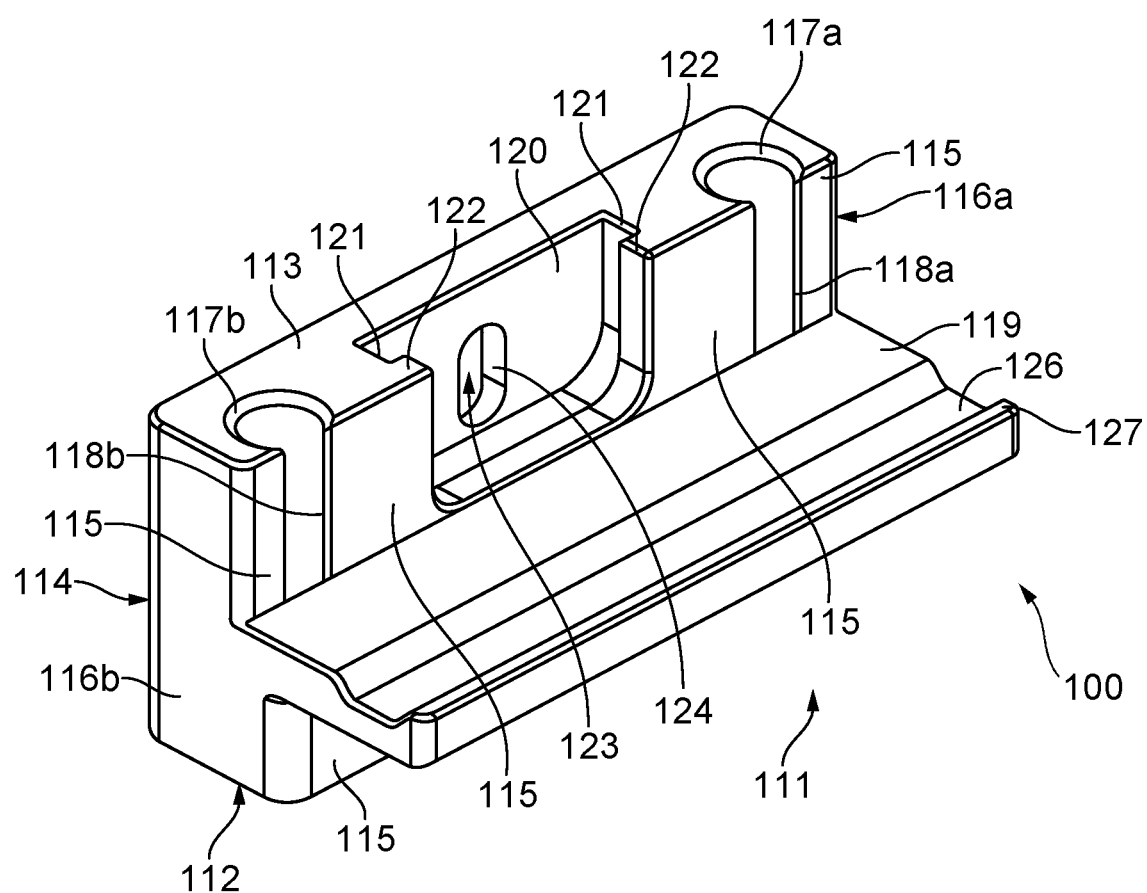
FIG. 9 illustrates a bottom, perspective view of a lower portion of the body of the clamp of the invention.
Figure 10A:
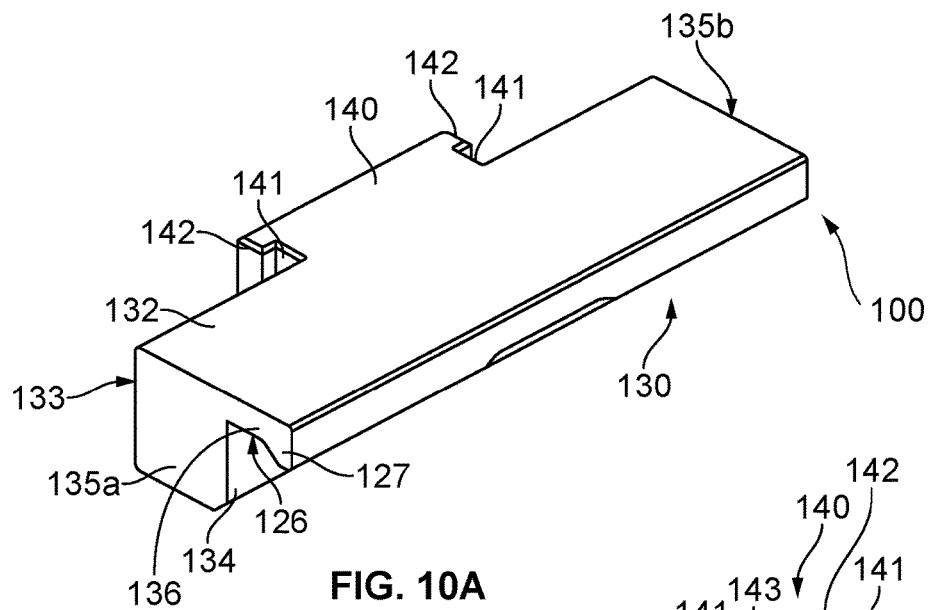
FIGS. 10A, 10B and 10C are expanded, perspective views illustrating a lower portion of the body of the clamp.
Figure 10B:
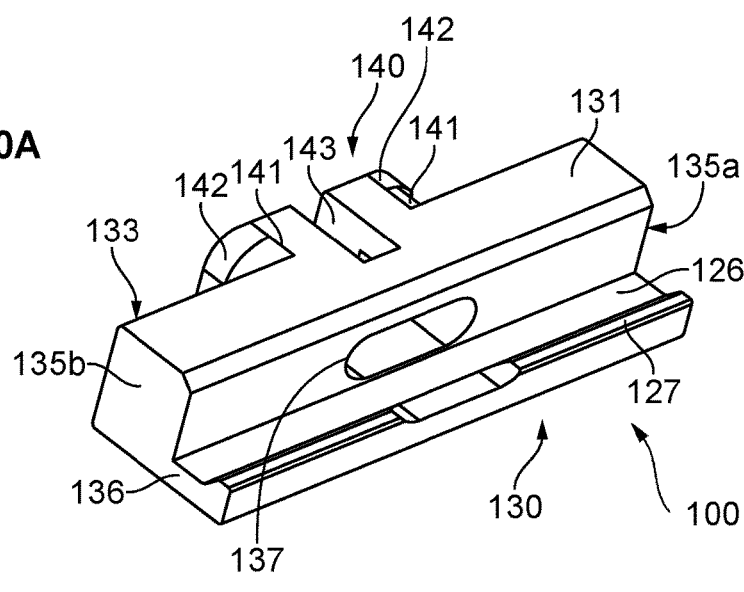
Figure 10C:
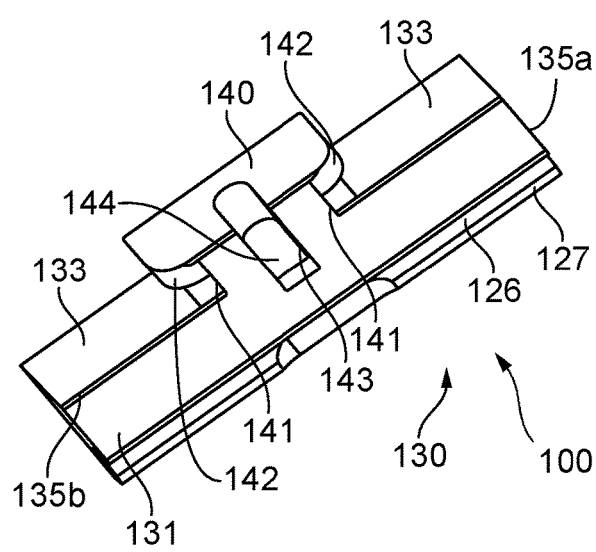

The clamp assembly 110 comprises an upper body portion 111 configured to operatively connect to a lower body portion 130. The fastener assembly 150 comprises a T-bar 151 with a threaded portion 152 configured to be disposed in openings of the upper body portion 111 and lower body portion 130 so as to join using forces applied by a washer assembly 160 and control assembly 170. Referring specifically to FIGS. 3, 8, and 9, the upper body portion 111 of the clamp assembly 110 comprises the top portion 112, a bottom portion 113, a front portion 114, a back portion 115 portion and side portion 116 that is designated as individual sides 116a and 116b.

The upper body portion 111 further comprises one or more openings 117 designated as openings 117a and 117b that can be formed between the top portion 112 and the bottom portion 113 extending therethrough. The openings 117a and 117b are configured to receive one or more posts 104 for attaching a patient positioner 103 to the side rail 102 of the support table 101 according to an embodiment of the invention. The upper body portion 111 also comprises one or more slot openings 118 designated as slot openings 118a and 118b. The slot openings 118a and 118b are configured to receive one or more posts 104 for attaching a patient positioner 103 to the side rail 102 of the support table 101 according to an embodiment of the invention. The clamp assembly 110 can be assembled such that the slot openings 118a and 118b can be located adjacent the slot recess 138 designated as slot recesses 138a and 138b to accomplish single action locking multiple components in different force factors.

Figure 6:
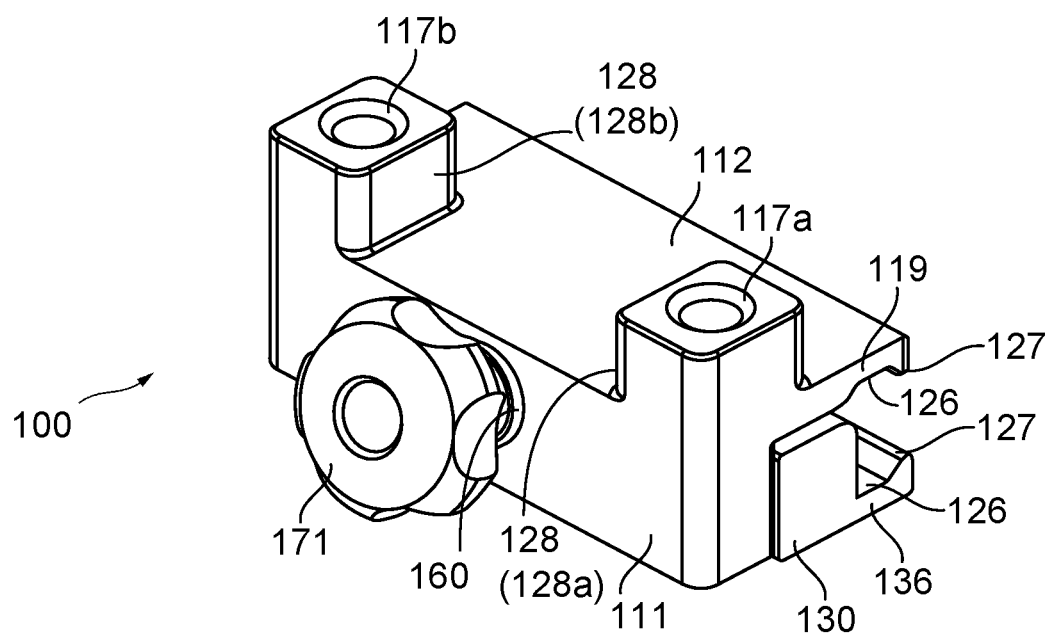
FIG. 6 illustrates a bottom, perspective view of another embodiment of a clamp of the invention.

The upper body portion 111 comprises a back portion 115 that can be configured with a side rail arm 119 that can further have a side rail register 126 and a side rail lip 127 so as to couple the clamp 100 to the side rail 102. The upper body portion 111 also comprises a channel portion 120 having a slot segment 121 and shoulder segment 122 adapted to be operably connected to and received by a key protrusion 140 and corresponding slot segment 141 and shoulder segment 142 that may be formed in the lower portion 130 of the clamp body assembly 110. Referring to FIG.6, in an alternative embodiment, top portion 112 of the upper body portion 111 may further comprise protrusions 128, designated as 128a and 128b, which may further have protrusion openings 117, designated as 117a and 117b, disposed therethrough to provide spacing, further structural support, strength, and integrity to the clamp 100.

The upper body portion 111 comprises one or more fastener openings 123 in the channel portion 120. The one or more fastener openings 123 can be formed in the top portion 112 and/or the front portion 114, and extend through to the back portion 115, so as to receive the fastener assembly 150 therein. Similarly, the lower portion 130 comprises one or more fastener head openings 137, such that operably connecting the channel portion 120 and the key protrusion 140 disposes the one or more fastener openings 123 and the one or more fastener head openings 137 in aligned relationship, such that the fastener assembly 150 may extend through the fastener opening 123, located in transverse slot 124, and extend from an arcuate, conical, or bowl-shaped recess 125. Furthermore, the washer assembly 160 may then be disposed on the threaded portion 152 of the T-bar 151 of the fastener assembly 150 extending therethrough, such that the control assembly 170 may be secured thereto, as shown in FIGS. 1, 2, 5, 6, 7A-7C, 8, 9, and 10A-10C.

As shown in FIGS. 1, 2, 4, 5, 6, 7A-7C, and 10A-10C, the lower portion 130 comprises a top portion 131, a bottom portion 132, a front portion 133, a back portion 134, and side portion 135 that is designated as individual sides 135a and 135b. The top portion 131 and front portion 133 comprise a key protrusion 140 extending therefrom. The key protrusion 140 comprises a slot segment 141 and a shoulder segment 142. The lower portion 130 of the clamp body assembly has a side arm 136 extending from the bottom portion 132 that may have a similar rail register 126 and side rail lip 127 for ease of registering on the side rail 102 of a support table 101. In one embodiment, the lower portion 130 further comprises one or more slot recess 138, designated as individual slot recess 138a and 138b, so as to form points of connection, along with slot openings 118a and 118b, configured to receive posts 104. The lower portion 130 further includes one or more fastener head openings 137 receiving the T-bar 151 of the fastener assembly 150 that can be located and formed by milled slot extending partially in the lower portion 130 between the front portion 132 and the back portion 134. Additionally, a transverse opening 143 can be formed in the top portion 131 and front portion 133 so as to allow the free travel of the fastener assembly 150 and angular displacement thereof to accomplish single action locking feature of the clamp 100 to connect multiple components in different force factors.

In this manner, the clamp assembly 110 can be assembled such that the slot openings 118a and 118b can be located adjacent respective slot recesses, 138a and 138b, to accomplish single action locking. By tightening the control assembly 170, which advances washer assembly 160 along threaded portion 152 of the fastener assembly 150 toward T-bar 151, the clamp 100 achieves different force factors where, for example, the upper portion 111 and lower portion 130 are forced in two directions simultaneously. Milled portion 144, in cooperation with arcuate recess 125 and conical portion 163, allow for angular movement of fastener assembly 150, thereby providing a clamping force to both the side rail 102 and to the posts 104, simultaneously.

Figure 2:
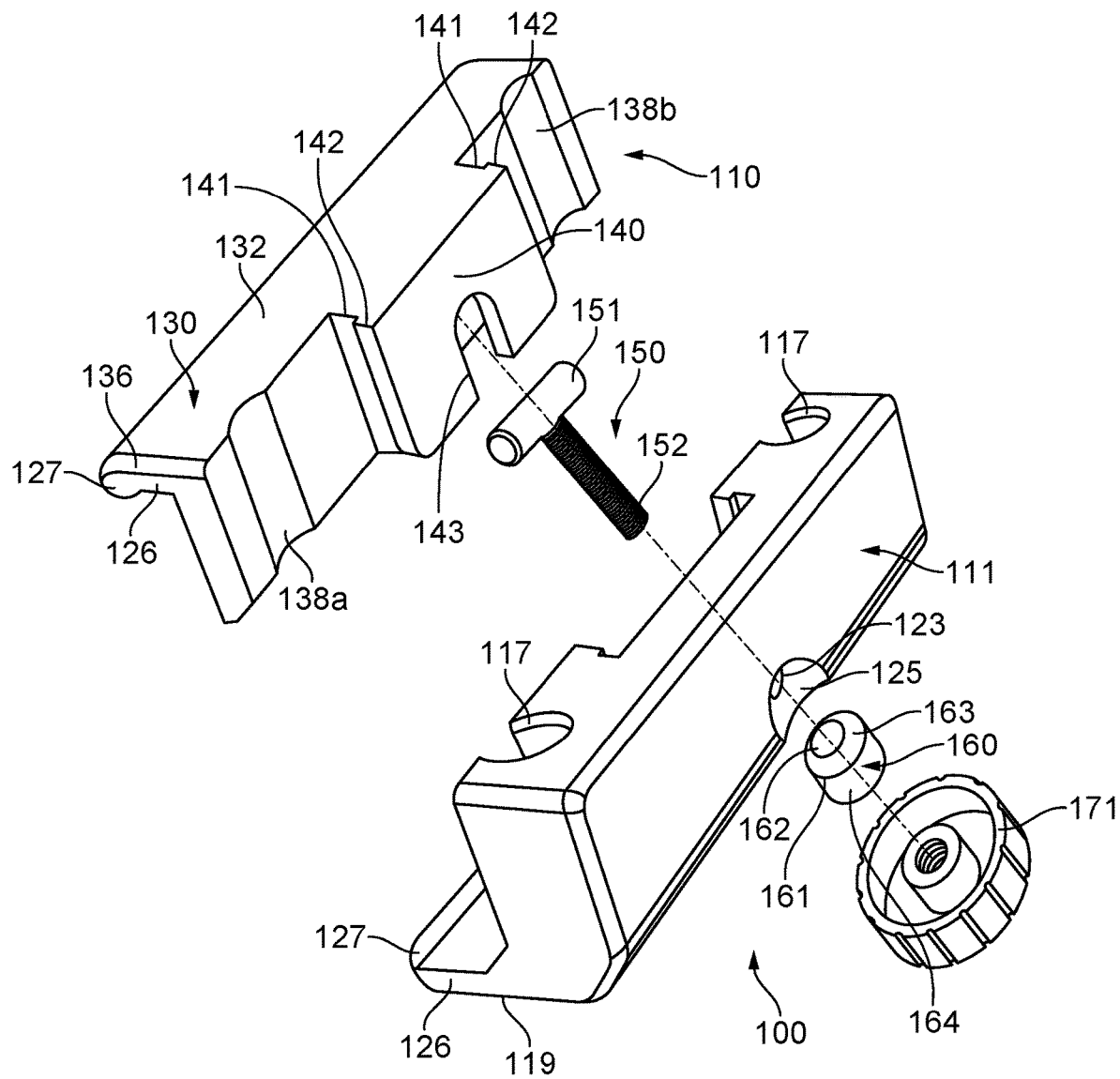
FIG. 2 illustrates an expanded, perspective view of the clamp of FIG. 1 of the invention.

As shown in FIG. 2, the fastener assembly 150 may comprise a T-bar 151 with a threaded portion 152. As shown in FIG. 7C, the fastener assembly 150 may alternatively comprise a T-segment 153, having an opening 154 centrally disposed along the shaft 157 of the T-segment 153. A post 158, which may be threaded 159, and may further be received by opening 154. T-segment 153 may further have a longitudinal opening 155, extending between side portions 156, so as to facilitate proper sterilization and/or cleaning, in an embodiment where the clamp is used for surgical procedures.

Furthermore, as shown in FIG. 7C, the washer assembly 160 comprises a body 161 having a centrally disposed opening 162 configured to receive the fastener assembly 150, specifically the threaded portion 152 of the T-bar 151 or the threaded portion 159 of the post 158 therein. The body 161 further has a surface portion 164, an interior portion 165, and a conical portion 163 configured to be received in the arcuate recess 125 and allow for smooth angular displacement by the tightening of the control assembly 170. In operation, tightening control assembly 170 forces the upper portion 111 and the lower portion 130 toward one another to achieve clamping forces in multiple directions, simultaneously: first, a clamping force may be achieved in a direction that allows upper and lower portions 111 and 130 to fixedly attach to, for example, rail 102; second, a clamping force may be achieved in a direction that allows upper and lower portions 111 and 130 to fixedly attach to, for example, post 104. As previously described, the mill portioned 144, in conjunction with arcuate recess 125 and conical portion 163, provide for angular movement that achieves simultaneous clamping of multiple components, by allowing the threaded portion 152 or post 158 to move in an angular manner. Referring to FIGS. 1, 2, 5, 6, and 7A-7C, the control assembly 170 may be a knob 171, which may further have a threaded attachment to receive the threaded portion 152 of an opposite end of the T bar 151 for the threaded portion 159 of the post 158 for the T-segment 153. It is to be appreciated by those of skill in the art that any armature that provides for the tightening and loosening by the threads would be suitable to use in may offer additional advantages.

Relative dimensions of the components that comprise clamp 100 may vary depending on the purpose served, for example, clamping the side rail 102 and clamping to the posts or pins 104. However, clamp assembly 110, fastener assembly 150, washer assembly 160, and control assembly 170 may be dimensioned differently for another application, such as clamping objects to the standing seam of a metal roof. In the first example, primary clamping is to be performed to operably connect the clamp body assembly 110 to the side rail 102 by the arms 119 and 136 being pulled together by the tightening of the control assembly 170 advancing on the threaded fastener portion 152 or 159 and pressing the washer assembly against the upper portion 110. Once the side rail 102 is compressed by the arms 119, 136, e.g. in the vertical plane, advancing the knob 171 on the threads 152, 159 moves the fastener assembly 150 in the openings of the channel portion 120 and key portion 140, whereby the flexibility and rotatable conical portion 163 of the washer 160 in the arcuate recess allows the fastener to move along the transverse slot 143 and milled portion 144 to compress the back portion 155 of the upper portion 111 towards the back portion 134 of the lower portion 130 of the clamp body assembly 110. This action secures the posts 104 in the openings 117 (117a, 117b), and the portions of posts 104 that protrude from the slot openings 118 (118a, 118b) are engaged by the slot recesses 138 (138a, 138b), thereby achieving a compressing effect in the horizontal plane. Consequently, the clamp 100 balances and equalizes multiple forces by varying the angle of advancement of the threaded portion 152 (or threads 159 of post 158) relative to upper and lower body portions 111, 130, which achieves clamping in multiple directions. The directions in which clamping is effectuated may be mutually orthogonal, wherein compressing forces act in the horizontal and vertical direction, or alternatively compressing forces may act in non-orthogonal, but offset, directions, depending on the application. As described, angular rotation of the fastener assembly 150 relative to the upper and lower body portions 111, 130 allow for these offset clamping forces to be achieved using a single-point control, such as via control assembly 170.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clamp for coupling one or more devices to a structure, the clamp comprising:
   an upper body including:
      an upper rail arm extending outwardly from said upper body and adapted to couple to an upper surface of the structure,
      one or more upper body fastener openings extending through said upper body, and
      one or more upper body device openings extending through said upper body, each of said one or more upper body device openings including a slot opening;
   a lower body including a back portion, wherein said one or more upper body device openings and said back portion are adapted to receive the one or more devices,
      a lower rail arm extending outwardly from said lower body and adapted to couple to a lower surface of the structure, and
      one or more lower body fastener openings extending through said lower body;
   a fastener assembly disposed in and extending through each of said one or more upper and lower body fastener openings, said fastener assembly being adapted to apply a multidirectional force in a first direction to said upper and lower bodies, whereby a decomposition of the multidirectional force is applied in a second direction and in a third direction such that:
      said second direction is applied to move said upper and lower arms to clamp the structure, and said third direction is applied to move said one or more upper body device openings and said back portion to clamp the one or more devices; and a control assembly adapted for operably coupling to said fastener assembly, such that said control assembly and said fastener assembly are adapted to provide simultaneous, multidirectional clamping characterized by said second and third directions.

2. The clamp according to claim 1, wherein said second and third directions are oriented with respect to one another at an angle selected from the group consisting of orthogonal, acute, and obtuse.

3. The clamp according to claim 1, wherein the one or more devices comprises one or more surgical devices.

4. The clamp according to claim 1, wherein the one or more devices is/are one or more building structures selected from the group consisting of a solar panel, a snow rail system, HVAC equipment and electrical equipment.

5. The clamp according to claim 1, wherein the structure is a surgical support.

6. The clamp according to claim 5, wherein said surgical support is a side rail of an operating table.

7. The clamp according to claim 1, wherein the structure is a building structure.

8. The clamp according to claim 7, wherein the building structure is a standing seam of a metal roof.

9. The clamp according to claim 1, the clamp further comprising:

a channel portion extending into said upper body proximate a portion of said one or more upper body fastener openings, and a key protrusion extending outwardly from said back portion of said lower body proximate a portion of said one or more lower body fastener openings, wherein said channel portion and said key protrusion form complementary shapes such that, in an assembled configuration and upon tightening of said control assembly about said fastener assembly, said channel portion and said key protrusion facilitate the moving of said upper body toward said lower body along said first direction, to provide simultaneous, multidirectional clamping characterized by said second and third directions.

\* \* \* \* \*